United States Patent
Linder et al.

(10) Patent No.: US 6,505,072 B1
(45) Date of Patent: Jan. 7, 2003

(54) IMPLANTABLE ELECTRONIC STIMULATOR HAVING ISOLATION TRANSFORMER INPUT TO TELEMETRY CIRCUITS

(75) Inventors: William J. Linder, Golden Valley, MN (US); Mark D. Amundson, Cambridge, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 257 days.

(21) Appl. No.: 09/714,337

(22) Filed: Nov. 16, 2000

(51) Int. Cl.$^7$ ................................................. A61N 1/08
(52) U.S. Cl. ............................. 607/32; 607/60; 128/903
(58) Field of Search ............................. 607/4, 5, 9, 12, 607/14, 30, 32, 60; 128/903

(56) References Cited

U.S. PATENT DOCUMENTS

| | | | |
|---|---|---|---|
| 4,194,179 A | * 3/1980 | Malinouskas | 128/903 |
| 4,440,172 A | 4/1984 | Langer | |
| 4,830,006 A | * 5/1989 | Haluska et al. | 607/4 |
| 4,880,004 A | * 11/1989 | Baker et al. | 607/4 |
| 5,324,315 A | * 6/1994 | Grevious | 607/32 |
| 5,342,408 A | 8/1994 | deCoriolis et al. | |
| 5,470,341 A | * 11/1995 | Kuehn et al. | 607/5 |
| 5,534,018 A | * 7/1996 | Wahlstrand et al. | 607/9 |
| 5,725,561 A | * 3/1998 | Stroebel et al. | 607/9 |
| 6,094,597 A | 7/2000 | Wold | |
| 6,115,636 A | 9/2000 | Ryan | |
| 6,249,703 B1 | * 6/2001 | Stanton et al. | 607/32 |

* cited by examiner

*Primary Examiner*—Willis R. Wolfe
(74) *Attorney, Agent, or Firm*—Thomas J. Nikolai; Nikolai & Mersereau, P.A.

(57) ABSTRACT

An implantable medical device for applying electrical stimulating pulses to body tissue in which the device includes a hermetically sealed metal housing that contains the stimulating pulse delivery circuitry as well as a telemetry transmitter and telemetry receiver and where the metal housing serves as a return electrode. An isolation transformer is operatively coupled between an antenna/coil used to receive and transmit information from and to an external programmer device and the telemetry receiver and telemetry transmitter within the implanted device. The isolation transformer effectively precludes high voltage stimulating pulses from causing damage to the telemetry circuit components.

19 Claims, 4 Drawing Sheets

IMPLANTABLE ELECTRONIC STIMULATOR HAVING ISOLATION TRANSFORMER INPUT TO TELEMETRY CIRCUITS

BACKGROUND OF THE INVENTION

I. Field of the Invention

This invention relates generally to implantable medical tissue stimulating apparatus, and more particularly to a programmable implantable medical device having an electronic therapy delivery circuit and a telemetry system for allowing duplex communication between the implanted therapy delivery circuit and an external programmer where the implanted telemetry transmitter and receiver circuits are effectively isolated from the output of the therapy delivery circuit to thereby prevent damage to the telemetry transmitter and receiver circuits.

II. Discussion of the Prior Art

Implantable medical stimulating devices, such as Automatic Implantable Cardiac Defibrillators (AICD), typically comprise a hermetically sealed housing or enclosure made of titanium or other suitable metal that is body compatible and moisture impervious. Contained within the housing is electronic circuitry for monitoring cardiac activity and a therapy delivery circuit for producing tissue stimulating pulses under control of a programmable microprocessor. The enclosure of these implantable medical devices will also typically include a telemetry transmitting circuit and a telemetry receiving circuit, allowing two-way communication with an external programmer.

Affixed to the exterior of the housing of these prior art implantable devices is a molded plastic header having one or more lead receiving bores formed longitudinally therein. The bores are provided with electrical contacts for mating with corresponding contacts on the proximal end of an elongated, flexible therapy delivery lead of the type having tissue contacting electrodes at the distal end thereof. The electrodes are connected to the contacts on the proximal end of the lead by means of conductors extending through the insulative lead body, all as is well known in the art.

The header may also support either an antenna or an electromagnetic coil as a transducer used to transmit and receive data being telemetered to and from the implantable device. To establish a connection between the sensing circuitry, the therapy delivery circuitry and the telemetry transmitter and receiver within the housing and the lead contacts and the transducer on the header, hermetically sealed feed-through pins are typically provided that extend through insulating seals mounted in the enclosure beneath the header to contact points within the header to which the lead barrel contacts and the telemetry antenna/coil connect. Typical feed-through devices are described in U.S. Pat. No. 5,333,095. Because of their cost and complexity, the number used in a device is to be minimized.

Biomedical devices, particularly implantable medical devices, such as cardiac defibrillators, can impress very large shocking energies on the patient to thereby resynchronize heart function. In some defibrillator designs, the titanium enclosure or housing is used in combination with a lead electrode as an opposing electrode in applying this high-energy stimulation. The term "Hot Can" has been used to describe this lead electrode-to-case stimulation approach. Because the implantable device's external casing is used as an electrode, much of the circuitry enclosed thereby cannot use the case as a voltage reference point, such as a ground reference point, like many other implantable devices. Failure to adequately isolate the telemetry circuitry from Hot Can shocks can cause electrical damage to the telemetry transmitter and receiver and this can adversely impact the ability of the device to also apply shocking therapy when needed. Such isolation is also necessary to insure that other devices, such as pacemakers, located in proximity to a defibrillator are not damaged by high-energy shocking potentials.

Most prior art telemetry systems used with implantable medical devices utilize magnetic or electromagnetic fields to perform the transfer of data from the implantable device to an external programming device for clinician or patient use. Magnetic field telemetry uses an inductive coil disposed in a wand and placed over the site of the implantable device to magnetically couple to a receiving coil either within the header or within the enclosure of the implanted unit. In the case of electromagnetic field telemetry, an antenna in the external wand transmits RF energy to a corresponding antenna disposed in or on the header of the implanted unit.

As is explained in the deCoriolis et al. U.S. Pat. No. 5,342,408, it is advantageous to have the coil/antenna of the implantable device disposed outside of the metal housing to avoid the shielding losses that occur as the frequency of the RF telemetry carrier signal increases. The involvement of the housing in these higher frequency forms of telemetry becomes increasingly critical for two reasons. The first reason is that the case becomes a ground plane or shield to shape or control magnetic and electromagnetic field propagation. The second reason is that the case becomes a convenient circuit tie point, thereby avoiding the need for an additional costly feed-through assembly in the device. As those skilled in the art appreciate, feed-throughs are structures to be minimized in implantable devices since they become entry points for electro-magnetic interference and need to be designed with high electrical and mechanical precision to limit such interference.

A need therefore exists for a way to permit Hot Can therapy delivery in an implantable medical device that also incorporates telemetry circuits such that the telemetry circuits are effectively isolated from high shocking potentials while yet minimizing the number of feed-throughs employed for conductively connecting the therapy delivery circuit to the lead and the transmitting/receiving electronics to a coil/antenna disposed in or on the device's header.

SUMMARY OF THE INVENTION

The foregoing need is met in accordance with the present invention by providing an implantable medical device having a moisture impervious, body-compatible, metal housing containing a therapy delivery circuit, a telemetry transmitter and a telemetry receiver. Affixed to the metal housing of the device is an electrically non-conductive header which supports a magnetic or electromagnetic field energized telemetry coil/antenna. At least one hermetically sealed feed-through pin extends from the header where it is connected to the coil/antenna into the metal housing. Disposed within the housing is an isolation transformer having a primary winding and a first secondary winding where at least one terminal of the primary winding is coupled to the feed-through pin and the first secondary winding is coupled in circuit with at least one of the telemetry transmitter and telemetry receiver to permit signal flow between the transmitter or receiver and the telemetry coil/antenna. The isolation transformer serves to electrically isolate the telemetry transmitter or receiver from voltages impressed on the housing by the therapy delivery circuit.

The isolation transformer may have a further secondary winding where the first secondary winding connects to the telemetry transmitter and the other secondary winding connects to the telemetry receiver.

In another alternative embodiment, a two electrode therapy lead having an integral telemetry antenna connects to the device header for twin feed-through connection to an internal isolation transformer primary winding. In this arrangement, the therapy delivery circuit connects to these same two feed-through pins but signals from the therapy delivery circuit are attenuated by a high-pass filter before reaching the isolation transformer primary winding.

DESCRIPTION OF THE DRAWINGS

The foregoing features, objects and advantages of the invention will become apparent to those skilled in the art from the following detailed description of a preferred embodiment, especially when considered in conjunction with the accompanying is in which.

DESCRIPTION OF THE PREFERRED EMBODIMENT

Figure 1:
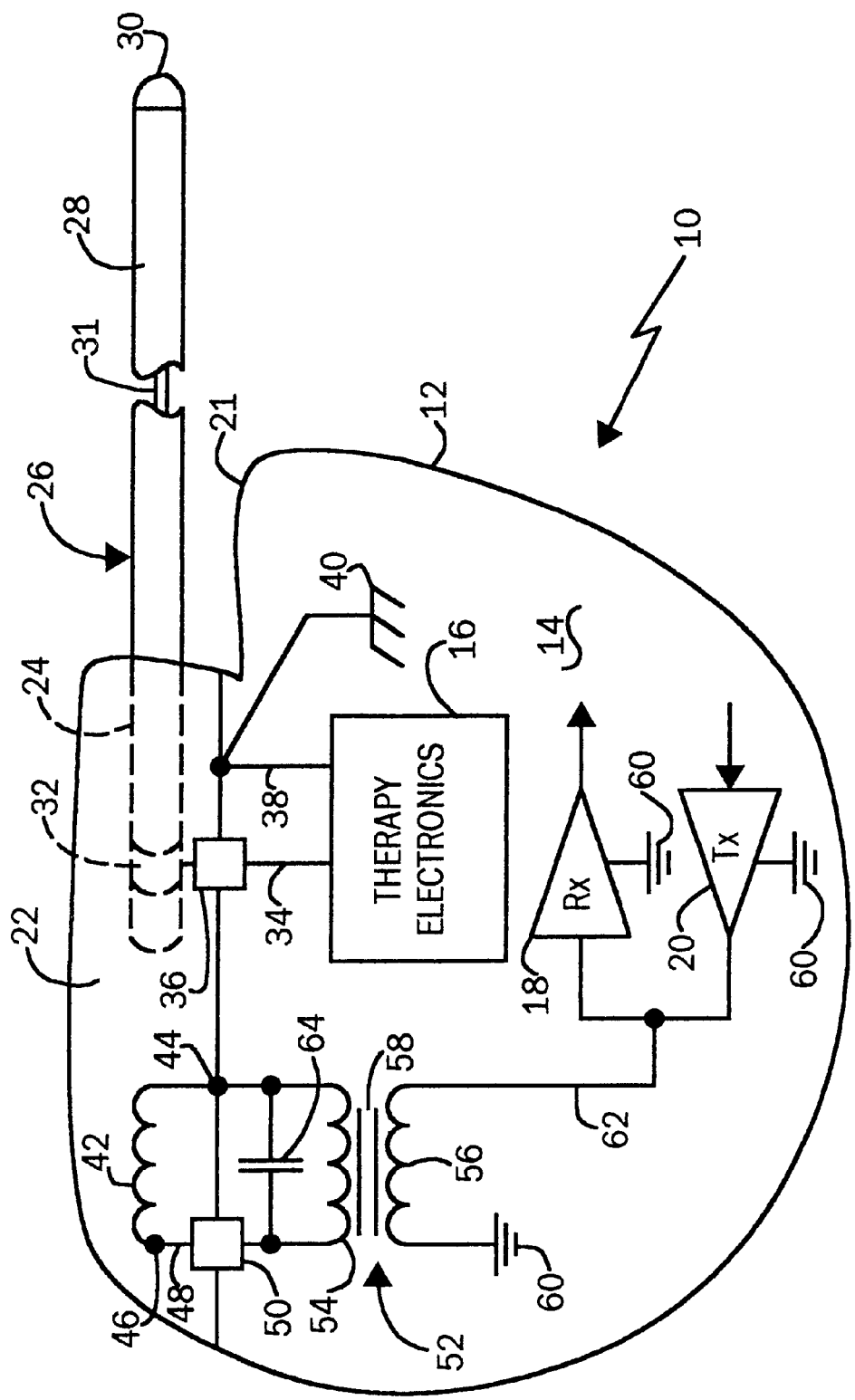
FIG. 1 is a schematic diagram illustrating a first embodiment of the invention incorporating an external header mounted telemetry coil and Hot Can therapy delivery.

Referring now to FIG. 1, it shows a schematic block diagram of an implantable medical device 10 constructed in accordance with a first embodiment of the present invention. The device 10 generally includes a moisture-impervious, body-compatible, metal housing 12 of known construction defining a hermetically sealed chamber 14 in which are disposed a therapy delivery circuit 16, a telemetry receiver circuit 18, and a telemetry transmitter circuit 20. Affixed to an upper planar surface 21 of the housing or can 12 is a header 22 formed of a suitable medical grade electrically insulating plastic. Formed longitudinally in the header 22 is a lead terminal receiving bore or socket 24 for receiving a proximal end portion of a therapy delivery lead 26. The lead 26 has an elongated, flexible lead body 28 having a conductive electrode 30 at a distal end thereof. The electrode 30 is connected to a contact ring 32 by an elongated flexible conductor 31 contained within the lead body 28. Contact ring 32 is designed to mate with a further electrical contact disposed in the bore 24 of the header 22.

A feed-through pin 34 passes through an insulating seal 36 disposed in the housing 12 and connects to the contact in the lead bore 24 to which the lead contact 32 mates. The therapy delivery circuit 16 also connects by a conductor 38 to the metal housing 12 which serves as a chassis ground, as indicated by the symbol 40.

With continued reference to FIG. 1, also mounted within the molded plastic header 22 is a telemetry coil 42. It has a first terminal connected to chassis ground by virtue of being electrically bonded to the metal housing 12 at a tie point 44. A second terminal of the coil 42 is bonded at 46 to a feed-through pin 48 which extends into the interior of the housing 12 by way of an insulating hermetic seal 50 that electrically insulates the feed-through pin 48 from the housing 12. The feed-throughs are constructed so as to incorporate filter capacitors in a manner somewhat like that described in the aforeferenced '095 patent.

In accordance with the present invention, there is provided an isolation transformer 52 having a primary winding 54 and a secondary winding 56 disposed on a ferrite core 58. As illustrated, the primary winding has one terminal thereof electrically bonded to the feed-through pin 48 within the housing 12 and its other terminal connects to the tie point 44 and is, therefore, at chassis ground.

The secondary winding 56 has one terminal thereof connected to a local ground, indicated by symbol 60, while the remaining terminal of the secondary winding is connected by way of a conductor 62 to an input of the telemetry receiver 18 and to an output of the telemetry transmitter 20.

Where the implantable medical device 10 is an AICD, the therapy electronics module 16 will sense cardiac depolarization signals developed between the electrode 30 and the can 12 and if predetermined rate or morphology criteria are met indicative of ventricular fibrillation, the therapy electronics 16 will function to deliver a shocking voltage between the lead electrode 30 and the can or housing 12, by way of feed-through pin 34, lead contact 32, the lead conductor 31 to the electrode 30.

The receiver 18 and the transmitter 20 are effectively isolated from this shocking potential by the inclusion of the isolation transformer 52. However, bi-directional communication between an external programmer (not shown) and the implanted receiver 18 may take place in the usual manner known in the art by positioning a telemetry wand (not shown) in proximity to the coil 42 and energizing the coil with digitally encoded data. The data is coupled, via the coil 42 in the header, causing pulse currents to flow through the primary winding 54 of the isolation transformer 52. By transformer action, the pulsitile information signals induced in the secondary winding 56 is applied, via conductor 62, to the input of the receiver 18. The output of the receiver 18 is ultimately applied to a microprocessor-based controller (not shown) that connects in controlling relation to the therapy electronics module 16. In a similar fashion, information to be transmitted from the microprocessor-based controller within the can 12 is applied as an input to the transmitter 20, which then is coupled through the isolation transformer 52 to the coil 42 and, thence, via the telemetry wand positioned over the implanted device, to the external programmer/monitor apparatus. Because the isolation transformer 52 effectively isolates the chassis ground 40 from the local or circuit ground 60, high voltage shocking pulses are not applied to the transmitting and receiving electronics, saving them from damage.

FIG. 1 also shows the inclusion of a capacitance element 64 in parallel with the primary winding 54 of the isolation transformer 52. This capacitance is chosen to provide impedance matching to thereby maximize the power transferred from the receiving coil 42 to the receiver 18 when in a receiving mode and from the transmitter 20 to the coil 42 when functioning in a transmitting mode. The capacitance element 64 need not be a discrete capacitor component but, instead, may be provided by appropriate consideration of the lead lengths, lead placement and inherent parasitic capacitance of the wiring and the transformer primary winding itself.

At first blush, one might reason that a device designer is creating his own problem by connecting one end of the transducer coil to chassis ground as at tie point 44 and that if he simply used two feed-throughs for the transducer coil 42, he could avoid using the isolation transformer entirely. There are at least two design issues associated with such an approach. First, there is the added cost factor involved with an additional feed-through. Feed-throughs tend to be fairly complex structures and, therefore, increase the cost for manufacturing and testing. A second reason is that feed-throughs generally incorporate noise filter capacitances, all as is explained in the aforereferenced U.S. Pat. No. 5,333,095. Given the presence of the feed-through capacitance, common mode signals in the form of a high current pulse from the charging of the feed-through capacitors appear in the circuit that needs to be protected. If an attempt is made to design a feed-through with a very low capacitance, one would end up with a further problem. That is, the feed-through is no longer performing its function of keeping unwanted RF noise out of the system. The feed-through filter capacitance is needed if one is to obtain the necessary resonance that will allow a narrow bandwidth at the high RF frequency used in the telemetry link. Stated somewhat differently, a level of capacitance is needed in the feed-throughs themselves and the capacitance cannot be made arbitrarily low.

Figure 2:
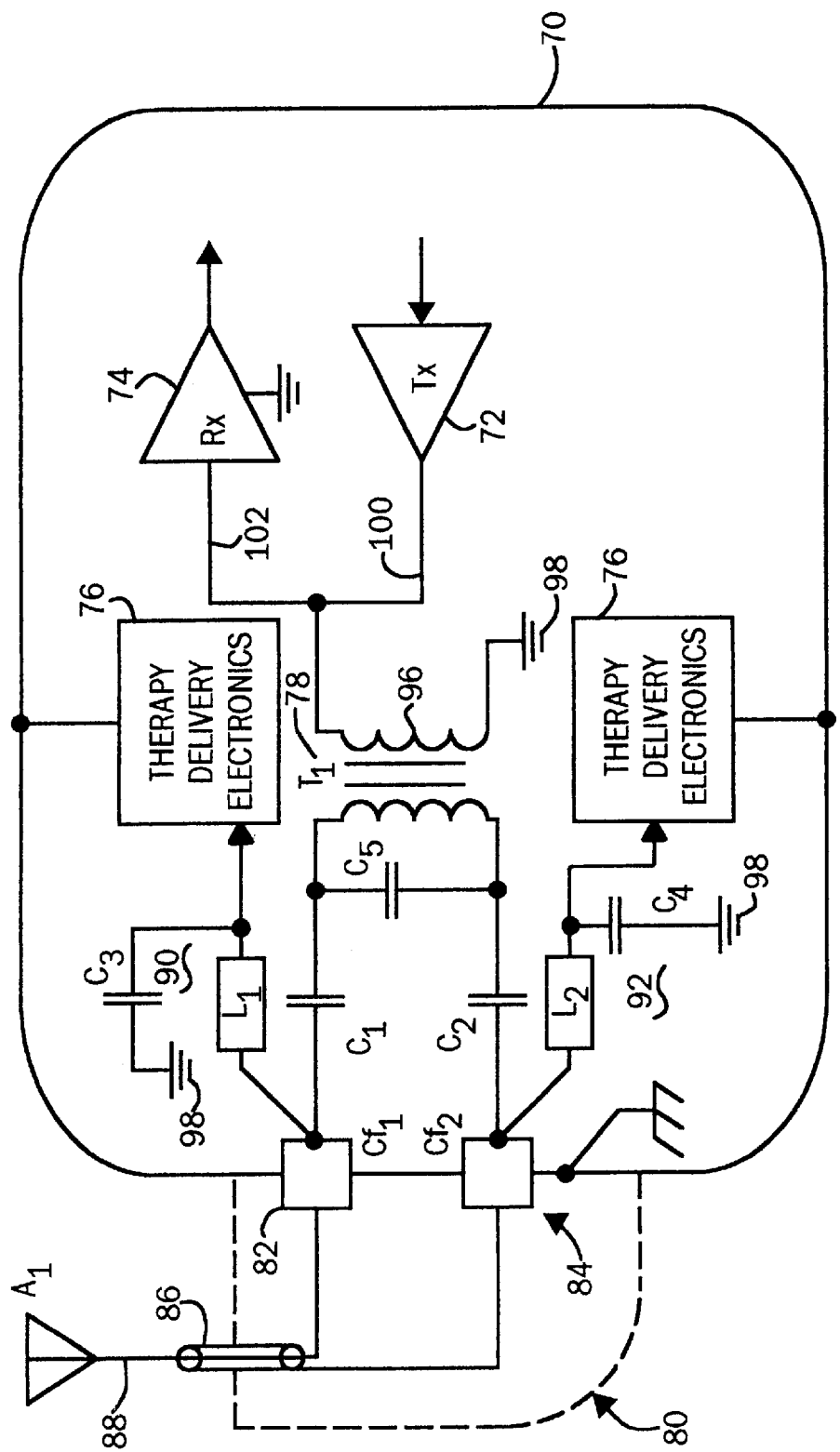
FIG. 2 is a schematic illustration of an alternative embodiment having a two-electrode lead with integral telemetry antenna.

With reference next to FIG. 2, there is illustrated a schematic electrical diagram of an implantable medical device incorporating an isolation transformer for effectively isolating the telemetry transmitter and receiver circuits from high voltages while still allowing the metal housing of the implanted device to serve as a return electrode for the therapy delivery circuit. The metal housing or can 70 contains, inter alia, a telemetry transmitter circuit 72, a telemetry receiver circuit 74, therapy delivery circuitry 76 and an impedance matching transformer 78. An insulating plastic header 80 is affixed to the can 70 and first and second feed-throughs 82 and 84 are mounted in the can 70 for providing a conductive connection between a lead 86 and the circuitry internal to the enclosure 70. The lead 86 is designed to contain an antenna wire 88 as a telemetry transducer.

The therapy delivery electronics 76 are operatively coupled by low-pass filter circuits 90 and 92 to the feed-through pins of the feed-throughs 82 and 84, respectively. Low-pass filter 90 includes a series inductance $L_1$ and a shunt capacitance $C_3$ connected to local ground 98. Low-pass filter 92 comprises series inductance $L_2$ and shunt capacitance $C_4$ also connected to local ground 98. These reactive components will typically not be discrete circuit elements, but instead, will result from the parasitic inductance and capacitance of the wiring and especially the layout or routing thereof Capacitances $C_1$ and $C_2$ serve as DC blocking capacitors preventing a DC current from flowing through the primary winding 94 of the isolation transformer 78. The capacitances $C_1$, $C_2$ and $C_5$ along with the inductance of the primary winding 94 function as a high-pass filter in the embodiment of FIG. 2.

The secondary winding 96 has one terminal thereof connected to circuit ground 98 and its other terminal connected, via conductors 100 and 102, to the output of the telemetry transmitter 72 and to the input of the telemetry receiver 74, respectively.

In operation, when a telemetry antenna is positioned in proximity to the implanted device and information is to be transmitted to the implanted device, a modulated RF signal is picked up by the antenna wire 88 and applied through feed-throughs 82 and 84 to the primary winding 94 of the isolation transformer 78. At the frequencies employed, the high-pass filter comprising capacitances $C_1$, $C_2$, $C_5$ and the inductance of the primary winding 94 do not significantly attenuate this signal. The low-pass filters 90 and 92, however, effectively block the transmitted signal from reaching the therapy delivery electronics 76. By transformer action, the transmitted signal is induced into the secondary winding 96 of the isolation transformer 78 and from there, via conductor 102, to the input of the receiver electronics 74.

When data is to be transmitted from the implanted medical device to the external programmer, the transmitter electronics 72 drives the secondary winding 96 of isolation transformer 78, causing the signal to be induced into the primary winding 94, and, thence, through the feed-throughs 82 and 84 to the transmitting antenna 88. The antenna radiates the RF signal to a receiving antenna in the telemetry wand used with the programmer.

Upon command from a microprocessor-based controller (not shown), the therapy delivery electronics 76 delivers a voltage pulse through low-pass filters 90 and 92 and the feed-throughs 82 and 84 to the lead 86 carrying a shocking electrode (not shown). The shocking voltage is relative to the grounded chassis comprising the metal housing 70. The high-pass filter comprising capacitors $C_1$, $C_2$, $C_5$ and the inductance of the primary winding 94 effectively attenuates the shocking signal precluding a voltage from being induced into the secondary winding 96 that would be of a magnitude that could damage the transmitter electronics 72 or the receiver electronics 74.

Figure 3:
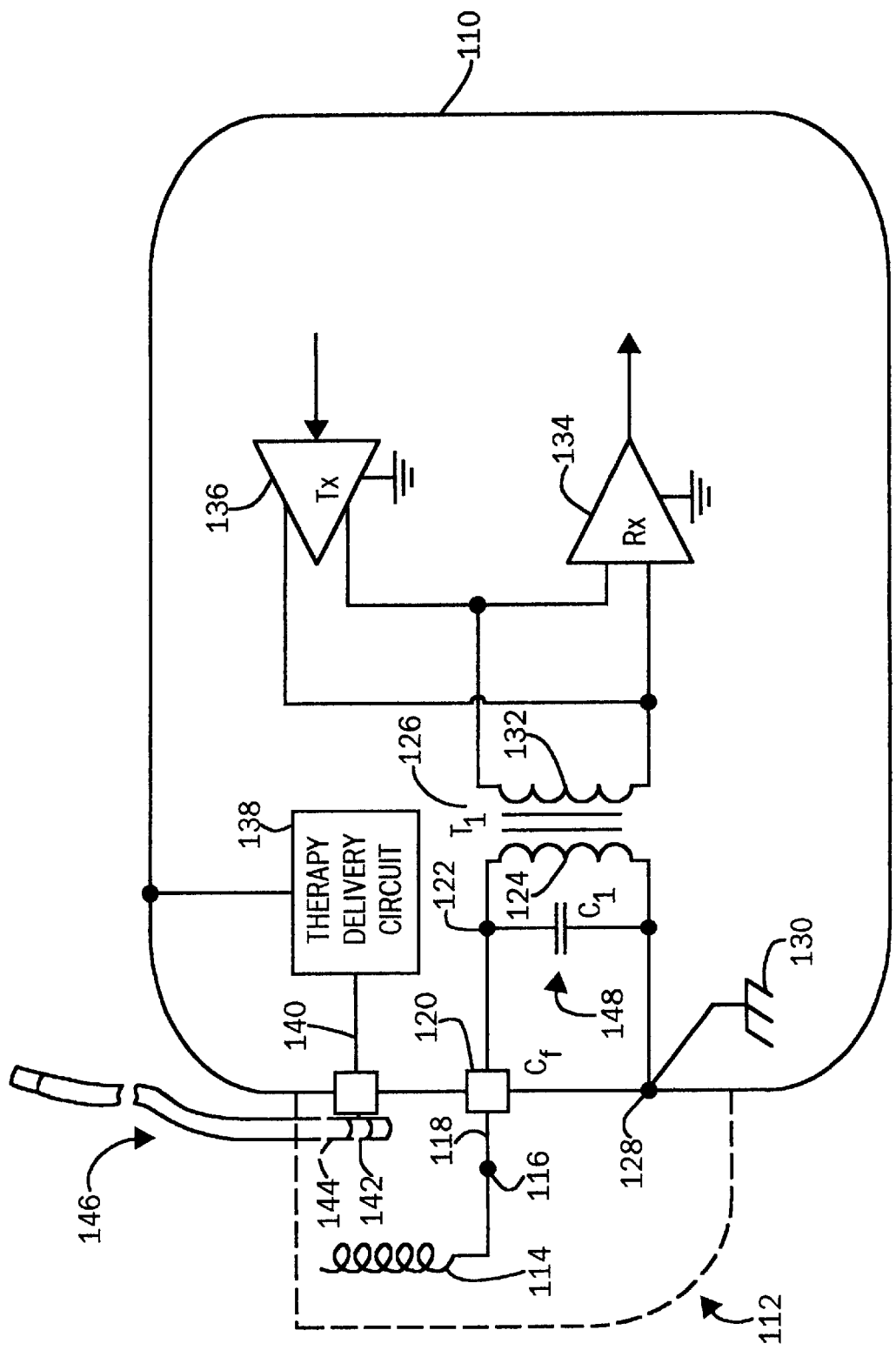
FIG. 3 is an electrical schematic diagram of yet a further embodiment showing a header-encapsulated antenna with a balun transformer for isolating the telemetry transmit and receiver circuits from high-energy stimulating signals.

Turning next to FIG. 3, there is illustrated yet another implementation of an implantable medical device utilizing an isolation transformer for protecting a telemetry transmitter and telemetry receiver from damage due to the administration of shocking potentials to a patient where the housing or can of the implantable medical device comprises a return for the shocking pulse. In FIG. 3, the implantable device's conductive metal can is identified by numeral 110 and, as in the earlier embodiments, affixed to the exterior of the can is a molded plastic header represented in dashed-line form and identified by numeral 112. Disposed within the body of the header 112 is a helical antenna coil 114. The terminal 116 of the antenna coil 114 is affixed to a feed-through pin 118 which passes through a hermetic seal 120 mounted in the can 110 into the interior thereof The feed-through pin 118 is connected at junction 122 to a first terminal of a primary winding 124 of a balun transformer 126. The remaining terminal of the primary winding 124 is connected to the can 110 at tie point 128 which is shown to be connected to chassis ground 130.

The secondary winding 132 of balun isolation transformer 126 provides a balanced connection to the inputs of the telemetry receiver 134 and to the outputs of telemetry transmitter 136.

The device of FIG. 3 is further shown to have a therapy delivery circuit 138 connected by a feed-through pin 140 to a lead terminal contact 142 disposed within a lead receiving bore 144 formed in the header 112. The contact 142 is adapted to mate with a terminal on the therapy delivery lead 146.

The primary winding of the balun-type isolation transformer 126 has a capacitance 148 connected in parallel with it. The capacitance of the feed-through 120 and that of the capacitor 148 form a resonance circuit with the inductance of the primary winding 124 to function as an impedance matching circuit to yield maximum power transfer between signal energy picked up by the antenna coil 114 and the receiver circuit 134. Likewise, the impedance matching circuit described functions to allow a maximum power transfer from the transmitter electronics 136 to the transmitting coil 114, via the balun transformer 126.

From the description of the previous embodiments, persons skilled in the art will appreciate that the incorporation of the isolation transformer 126 permits the metallic can 110 of the implantable medical device to be used as a return electrode for shocking voltages delivered by the therapy delivery circuit 138 to body tissue, via the lead 146, without introducing currents at damaging levels into the transmitter electronics 136 and/or the receiving electronics 134. The isolation transformer isolates the chassis ground 130 from local or circuit ground for the transmitter/receiver.

Figure 4:
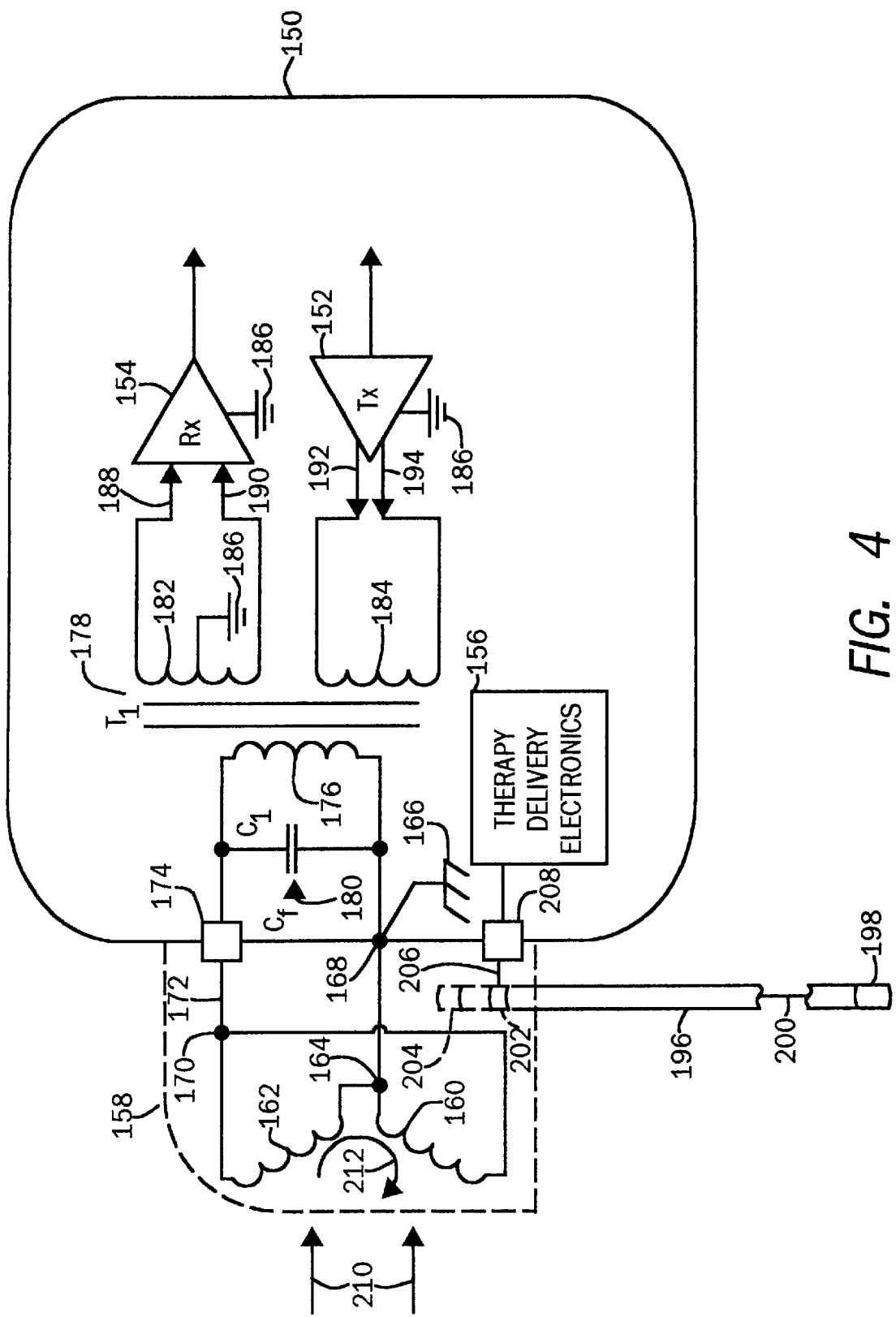
FIG. 4 is a schematic diagram of still another embodiment in which the isolating transformer has plural secondary windings individually connected to the telemetry transmitter and the telemetry receiver and a humbucking transducer coil in the header.

FIG. 4 illustrates yet another implementation of an implantable medical device in which an isolation transformer is advantageously used in a way that permits hot can therapy delivery without damage to sensitive telemetry circuitry. In this embodiment, the can or housing 150 encloses, inter alia, a telemetry transmitter 152, a telemetry receiver 154 and therapy delivery electronics 156. Also included, but not shown, would be the microprocessor-based controller that is adapted to receive cardiac depolarization signals via a lead located on or in the heart and to provide control signals to the therapy delivery electronics 156 when called for.

Affixed to the metal can 150 is a molded plastic housing indicated by the broken line 158. Disposed within the molded plastic heading 158 are first and second magnetic coils 160 and 162, each having one terminal thereof connected in common at a junction 164 that connects to chassis ground 166 at tie point 168. The opposing ends of coils 160 and 162 are connected in common at a junction 170 on a feed-through pin 172 passing through an opening in the can 150 that is hermetically sealed by an insulating feed-through seal member 174. The feed-through pin 172 also connects to one terminal of the primary winding 176 of an isolation transformer 178. A capacitance 180 is connected directly in parallel with the primary winding 176.

The isolation transformer 178 includes first and second secondary windings 182 and 184. The secondary winding 182 has a center tap connected to local circuit ground point 186 and the outer terminals thereof connect to inputs 188 and 190 of a telemetry receiver circuit 154. The secondary winding 184 is connected so as to be driven by the outputs 192 and 194 of the telemetry transmitter 152.

The therapy delivery electronics 156 connects between the metal can 150 which is at chassis ground, and a therapy delivery lead 196. This lead has a stimulating electrode 198 coupled by a lead conductor 200 to a proximal terminal contact 202. The contact mates with a further contact disposed within a lead receiving bore 204 formed in the header 158. This contact connects to a feed-through pin 206 of the feed-through device 208. The device 208 insulates the feed-through pin 206 from contact with the metal housing 150.

Considering next the operation of the embodiment of FIG. 4, the coils 160 and 162 in the header 158 are connected in humbucking relationship whereby far field ambient noise represented by arrows 210 are effectively canceled while near field signals from the telemetry wand and represented by arrow 212 induces a time varying voltage across the primary winding 176 of the isolating transformer 178. This signal couples into the secondary winding 182 of the transformer 178, thereby providing an input to the receiver electronics 154.

Likewise, when the telemetry link is requesting data from the implanted device, the telemetry transmitter 152 drives the secondary winding 184 to thereby induce a signal in the primary winding 178 and, via transducer coils 160 and 162, back to the pick-up winding in the telemetry wand (not shown).

In that the chassis ground 166 is isolated from the local circuit ground 186 through the inclusion of the isolation transformer 178, shocking potentials produced by the therapy delivery electronics are not fed into either the telemetry transmitter 152 or the telemetry receiver 154.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself

What is claimed is:

1. An implantable medical device comprising:
    (a) a moisture impervious, body compatible, metal housing containing a therapy delivery circuit, a telemetry transmitter and a telemetry receiver;
    (b) an electrically non-conductive header affixed to the metal housing and supporting a magnetic or electromagnetic field energized coil/antenna;
    (c) at least one hermetically sealed feed-through pin extending from the header into the metal housing and connected to the coil/antenna; and
    (d) an isolation transformer contained within the housing and having a primary winding and a first secondary winding, with at least one terminal of the primary winding being coupled to the at least one feed-through pin and the first secondary winding coupled in circuit with at least one of the telemetry transmitter and telemetry receiver to permit signal flow between the at least one telemetry transmitter or the telemetry receiver and the coil/antenna, the isolation transformer electrically isolating the at least one telemetry transmitter and telemetry receiver from voltages impressed on the housing by the therapy delivery circuit.

2. The implantable medical device of claim 1 and further including:
    a further terminal of the primary winding electrically connected to a chassis ground point on the metal housing and one terminal of the secondary winding being connected to a local ground point isolated from the metal housing.

3. The implantable medical device of claim 1 wherein the isolation transformer is a balun transformer with the secondary winding coupled to the input terminals of the telemetry receiver and to the output terminals of the telemetry transmitter.

4. The implantable medical device of claim 1 wherein the secondary winding is coupled in circuit with both the telemetry transmitter and the telemetry receiver.

5. The implantable medical device of claim 1 and further including a further hermetically sealed feed-through pin extending from the header into the metal housing and connected to the therapy delivery circuit.

6. The implantable medical device of claim 1 and further including a second secondary winding with the telemetry transmitter having output terminals coupled to the first secondary winding and the telemetry receiver having input terminals coupled to the second secondary winding.

7. The implantable medical device of claim 6 wherein the coil/antenna comprises first and second coil segments, each having a first terminal connected in common to the at least one feed-through pin and a second terminal connected in common to the metal housing.

8. The implantable medical device of claim 1 and further including a second hermetically sealed feed-through pin extending from the header into the metal housing and being coupled to the coil/antenna.

9. The implantable medical device of claim 8 wherein the primary winding has a further terminal coupled to the second hermetically sealed feed-through pin.

10. The implantable medical device of claim 9 wherein the at least one terminal and a further terminal of the primary winding are capacitively coupled individually to the at least one and the second hermetically sealed feed-through pins.

11. In an implantable medical device of the type having a hermetically sealed, body compatible electrically conductive housing for enclosing a therapy circuit, a telemetry transmitting circuit and a telemetry receiving circuit where the therapy circuit delivers relatively high voltage output signals between the conductive housing and a lead mounted electrode, a method of protecting the telemetry transmitting circuit and the telemetry receiving circuit from the relatively high output voltage, comprising the steps of
  (a) affixing a non-conductive header to the conductive housing, the header supporting a transmitting and receiving coil/antenna;
  (b) providing a hermetically sealed conductive feed-through including a conductive pin extending from the interior of the housing into the header;
  (c) connecting the conductive pin to the transmitting and receiving coil/antenna;
  (d) placing an isolation transformer within the housing, the isolation transformer having a primary winding with first and second terminals and a secondary winding with first and second terminals;
  (e) connecting the first terminal of the primary winding to the conductive pin within the housing and the second terminal of the primary winding to the housing; and
  (f) coupling at least one of the first and second terminals of the secondary winding to the telemetry transmitting circuit and the telemetry receiving circuit.

12. In an implantable medical device having a metal housing defining a sealed chamber and an insulating header affixed to the exterior housing, the chamber containing a therapy delivery circuit, a telemetry receiver and telemetry transmitter, a lead carrying an electrode and operatively coupled through a hermetically sealed feed-through pin extending between the header and the therapy delivery circuit within the housing for applying a stimulating voltage pulse between the electrode and the metal housing, and a telemetry coil supported by the header, the improvement comprising:
  an isolation transformer disposed within the housing, the isolation transformer having a primary winding coupled between a further feed-through pin and the metal housing and a secondary winding coupled between at least one of an input of the telemetry receiver and an output of the telemetry transmitter and a point of reference potential for the at least one telemetry receiver and telemetry transmitter such that the point of reference potential is conductively isolated from the stimulating voltage pulses.

13. An implantable medical device comprising:
  (a) a conductive metal housing defining a sealed chamber;
  (b) an insulating header affixed to an exterior portion of the housing and having a lead terminal receiving bore formed therein;
  (c) a therapy delivery circuit, a telemetry receiver, a telemetry transmitter, a telemetry transmitter contained within the housing;
  (d) an elongated, flexible lead body having a proximal end and a distal end with at least one electrode proximate the distal end of the lead body and connected by a conductor within the lead body to a lead terminal at the proximal end;
  (e) a first feed-through pin extending from the header into the sealed chamber, the first feed-through pin being connected to the therapy delivery circuit and to the lead terminal, when the lead terminal is inserted into the lead terminal receiving bore of the header;
  (f) a telemetry antenna/coil supported by the header and having a first terminal thereof connected to a second feed-through pin; and
  (g) an isolation transformer disposed within the sealed chamber and having a primary winding and a secondary winding, the primary winding being connected between the second feed-through pin and the metal housing and the secondary winding being coupled to at least one of the telemetry transmitter and telemetry receiver and a point of fixed potential.

14. The implantable medical device of claim 13 wherein the secondary winding is coupled to an input of the telemetry receiver, an output of the telemetry transmitter and to the point of fixed potential.

15. The implantable medical device of claim 13 wherein the isolation transformer includes first and second secondary windings with inputs of the telemetry receiver connected to the first secondary winding and the output of the telemetry transmitter connected to the second secondary winding.

16. The implantable medical device of claim 15 wherein the antenna/coil is a humbucking coil.

17. An implantable medical device comprising:
  (a) a conductive metal housing defining a sealed enclosure;
  (b) a therapy delivery circuit, a telemetry transmitter and a telemetry receiver contained within the enclosure;
  (c) an insulating header affixed to an exterior portion of the metal housing, the header having a lead terminal receiving bore formed therein;
  (d) a tissue stimulating lead having a proximal end and a distal end with at least one electrode proximate the distal end and a lead terminal at the proximal end, the lead terminal having contacts thereon electrically connected to the at least one electrode by a conductor, the conductor adapted to serve as a telemetry antenna;
  (e) first and second hermetically sealed feed-through pins extending between the lead terminal receiving bore, and the interior of the sealed enclosure and adapted to make electrical contact with contacts on the lead terminal when the lead terminal is inserted into the bore; and
  (f) an isolation transformer having a primary winding and a secondary winding, the primary winding being coupled to the first and second feed-through pins and the secondary winding having a first terminal connected to an input of the telemetry receiver circuit and an output of the telemetry transmitter and a second terminal to a point of fixed potential.

18. The implantable medical device of claim 17 and further including a high-pass filter connected in circuit with the primary winding of the isolation transformer for attenuating signals produced by the therapy delivery circuit.

19. The implantable medical device of claim 18 and further including a low-pass filter circuit coupled between the therapy delivery circuit and the first and second feedthrough pins for attenuating high frequency telemetry signals picked up by the telemetry antenna.

* * * * *